United States Patent
Mande et al.

(10) Patent No.: US 9,342,653 B2
(45) Date of Patent: May 17, 2016

(54) IDENTIFICATION OF RIBOSOMAL DNA SEQUENCES

(75) Inventors: Sharmila S. Mande, Andhra Pradesh (IN); Mohammed Monzoorul Haque, Andhra Pradesh (IN); Tarini Shankar Ghosh, Andhra Pradesh (IN); Sudha Chadaram, Andhra Pradesh (IN); Venkata Siva Kumar Reddy Chennareddy, Andhra Pradesh (IN)

(73) Assignee: Tata Consultancy Services Limited (IN)

( * ) Notice: Subject to any disclaimer, the term of this patent is extended or adjusted under 35 U.S.C. 154(b) by 1131 days.

(21) Appl. No.: 13/115,553

(22) Filed: May 25, 2011

(65) Prior Publication Data

US 2011/0295519 A1    Dec. 1, 2011

(30) Foreign Application Priority Data

May 26, 2010   (IN) .......................... 1629/MUM/2010

(51) Int. Cl.
*G06F 19/10* (2011.01)
*G06F 19/24* (2011.01)
*G06F 19/22* (2011.01)

(52) U.S. Cl.
CPC ................ *G06F 19/24* (2013.01); *G06F 19/22* (2013.01)

(58) Field of Classification Search
None
See application file for complete search history.

(56) References Cited

PUBLICATIONS

Diaz et al. (BMC Bioinformatics (2009) vol. 10:56, pp. 1-16).*
Haque (Bioinformatics (2009) vol. 25:14, pp. 1722-1730).*
Huson et al. (Genome Research (2007) vol. 17, pp. 377-386).*
Richter et al. (PLoS One (2008) vol. 3, pp. e3373 (1-12).*
Cole. et al. (Nucleic Acids Research (2009) vol. 37, pp. D141-D145).*
Huang et al. (Bioinformatics (2009) vol. 25, pp. 1338-1340).*
Wang et al. (Applied and Environmental Microbiology (2007) vol. 73, pp. 5261-5267).*
Chaffron et al. (Genome Research (2010) vol. 20:947-95).*
Keller et al. (IEEE Transactions on Systems, Man, and Cybernetics (1985) vol. SMC-15:580-585).*
Sandberg et al. (Genome Research (2001) vol. 11:1404-1409).*
Y. Huang et al: "Identification of ribosomal RNA genes in metagenomic fragments", Bioinformatics, vol. 25, No. 10, Apr. 3, 2009, pp. 1338-1340, XP55007711, ISSN: 1367-4803, DOI: 10.1093/bioinformatics/btp161 *abstract* * p. 1338.
K. Lagesen et al: RNAmmer: consistent and rapid annotation of ribosomal RNA genes n, Nucleic Acids Research, vo 1.35, No. 9, Jan. 1, 2007, pp. 3100-3108, XP55005462, ISSN: 0305-1048, DOI: 10.1093/nar/gkm160 *abstract* * p. 3100-p. 3102 *.
Meyer F et al: "The metagenomics RAST 1-15 server: a public resource for the automatic phylogenetic and functional analysis of metagenomes", BMC Bioinformatics, Biomed Central, London, GB, vol. 9, No. 1, Sep. 19, 2008, p. 386, e-pp. 1-8, XP021041778, ISSN: 1471-2105, DOI: 10.1186/1471-2105-9-386 *abstract*.
Diaz Naryttza N et al: "TACOA: Taxonomic classification of environmental genomic fragments using a kernelized nearest neighbor approach", BMC Bioinformatics, Biomed Central, London, GB, vol. 10, No. 1, Feb. 11, 2009, p. 56, XP021047319, e-pp. 1-16 ISSN: 1471-2105, DOI: 10.1186/1471-2105-10-56.
Gail L. Rosen et al: "Signal Processing for Metagenomics: Extracting Information from the Soup", Current Genomics, val. 10, Jan. 1, 2009, pp. 493-510, XP55007709, *p. 495-p. 498*.
Mohammed et al. "Eu-Detect: An algorithm for detecting eukaryotic sequences in metagenomic data sets", Journal of Biosciences, vol. 36, No. 4, Sep. 1, 2011, pp. 709-717, XP55007581, ISSN: 0250-5991.
Clarridge, JE. (2004) 3rd Impact of 16S rRNA gene sequence analysis for identification of bacteria on clinical microbiology and infectious diseases. Clin Microbiol Rev., 17:840-62.
Cole, J. R., Wang, Q., Cardenas, E., Fish, J., Chai, B., Farris, R. et al. (2009) The Ribosomal Database Project: improved alignments and new tools for rRNA analysis. Nucl. Acids Res, vol. 37(Database issue), D141-D145.

* cited by examiner

*Primary Examiner* — Lori A Clow
(74) *Attorney, Agent, or Firm* — Schwegman, Lundberg & Woessner, P.A.

(57) ABSTRACT

Method(s) for identifying rDNA sequences from a sample containing plurality of unknown DNA sequences are described herein. The method includes selecting one or more target clusters, from a plurality of reference clusters, corresponding to the query sequence. The target clusters are selected based on a composition based analysis. A proportion of probable rDNA clusters from the target clusters is identified. Based on the proportion of the probable rDNA clusters, the query sequence is identified as an rDNA.

17 Claims, 4 Drawing Sheets

IDENTIFICATION OF RIBOSOMAL DNA SEQUENCES

CLAIM OF PRIORITY

The present patent application claims the benefit of priority under 35 U.S.C. §119 to Indian Patent Application No. 1629/MUM/2010, filed May 26, 2010, the entire contents of which is incorporated herein by reference in its entirety.

TECHNICAL FIELD

The present subject matter relates, in general, to deoxyribonucleic acid (DNA) sequences and, in particular, identification of ribosomal DNA (rDNA) sequences.

BACKGROUND

Generally, ribosomal DNA sequences, such as 16S rDNA, are conserved across all bacterial and archaeal species and therefore, ribosomal DNA sequences are analyzed for estimating taxonomic diversity of a given environmental sample, such as a metagenome. Subsequent to analysis, enumeration of the number of ribosomal DNA sequences assigned to various taxonomic groups, such as species, genus, family, order, class or phylum, helps in quantifying the relative abundance of various organisms or taxa present in the environmental sample.

Since, the analysis of the ribosomal DNA sequences is expected to provide a comprehensive snapshot of taxonomic diversity, a majority of projects spend considerable resources (in terms of time, cost, and labor) in carrying out experiments that amplify, clone, and sequence ribosomal DNA sequences present in a given environmental sample. The ribosomal DNA sequences obtained from these experiments are then analyzed to get estimates of taxonomic diversity. In order to further characterize the given environmental sample, the entire genomic content of the environmental sample under study is subsequently extracted, fragmented, and sequenced. Millions of DNA sequences, originating from the genomes of various microbes in the environmental sample, are thus obtained. Given that the entire genomic content of an environmental sample is fragmented and sequenced, a subset of these sequenced DNA fragments corresponds to partial and complete portions of ribosomal gene sequences originating from various organisms in that sample. This subset of DNA fragments can thus be referred to as ribosomal DNA fragments.

With the recent advance in technology, and availability of faster and cheaper sequencing techniques, the taxonomic diversity of an environmental sample can alternatively be ascertained by identifying and subsequently analyzing these ribosomal DNA fragments. Obtaining estimates of taxonomic diversity using this alternative approach, therefore, does not depend on experimental procedures related to amplification, cloning, and sequencing of ribosomal DNA sequences. Instead, it depends on the following two factors. First is the cost of fragmenting and sequencing the entire genomic content of an environmental sample. Second is the efficiency of the 'in silico' method that is employed for identification of ribosomal DNA fragments from amongst the entire set of DNA fragments (obtained by fragmenting and sequencing the entire genomic content of an environmental sample). Given the current availability of efficient and cost effective sequencing technologies, the applicability of the 'alternative approach' thus depends to a large extent on the availability of in silico techniques, that can efficiently identify ribosomal DNA fragments from amongst the entire set of DNA fragments. Employing such in silico techniques is thus expected to save considerable amounts of time, efforts, and cost.

However, currently available in silico techniques for identification of ribosomal DNA sequences amongst millions of DNA sequences are not efficient in terms of computational time and sensitivity. Consequently, these in silico techniques have found little or no application in projects for direct identification of ribosomal DNA sequences from the sequenced genomic content of a given environmental sample.

SUMMARY

This summary is provided to introduce concepts related to identification of partial or complete ribosomal deoxyribonucleic acid (rDNA) sequences from a sample containing unknown DNA sequences, which are further described below in the detailed description. This summary is not intended to identify essential features of the claimed subject matter nor is it intended for use in determining or limiting the scope of the claimed subject matter.

Method(s) and a system(s) for identification of rDNA sequences from a sample containing a plurality of unknown DNA sequence are described herein. In one implementation, one or more target clusters, from amongst a plurality of reference clusters, corresponding to a query sequence are selected. The target clusters may be selected based on a composition based analysis. Subsequent to selection of the target clusters, the proportion of pre-tagged 'probable rDNA clusters' within the selected target clusters is determined. Based on the proportion of probable rDNA clusters, the query sequence is identified as the rDNA sequence.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
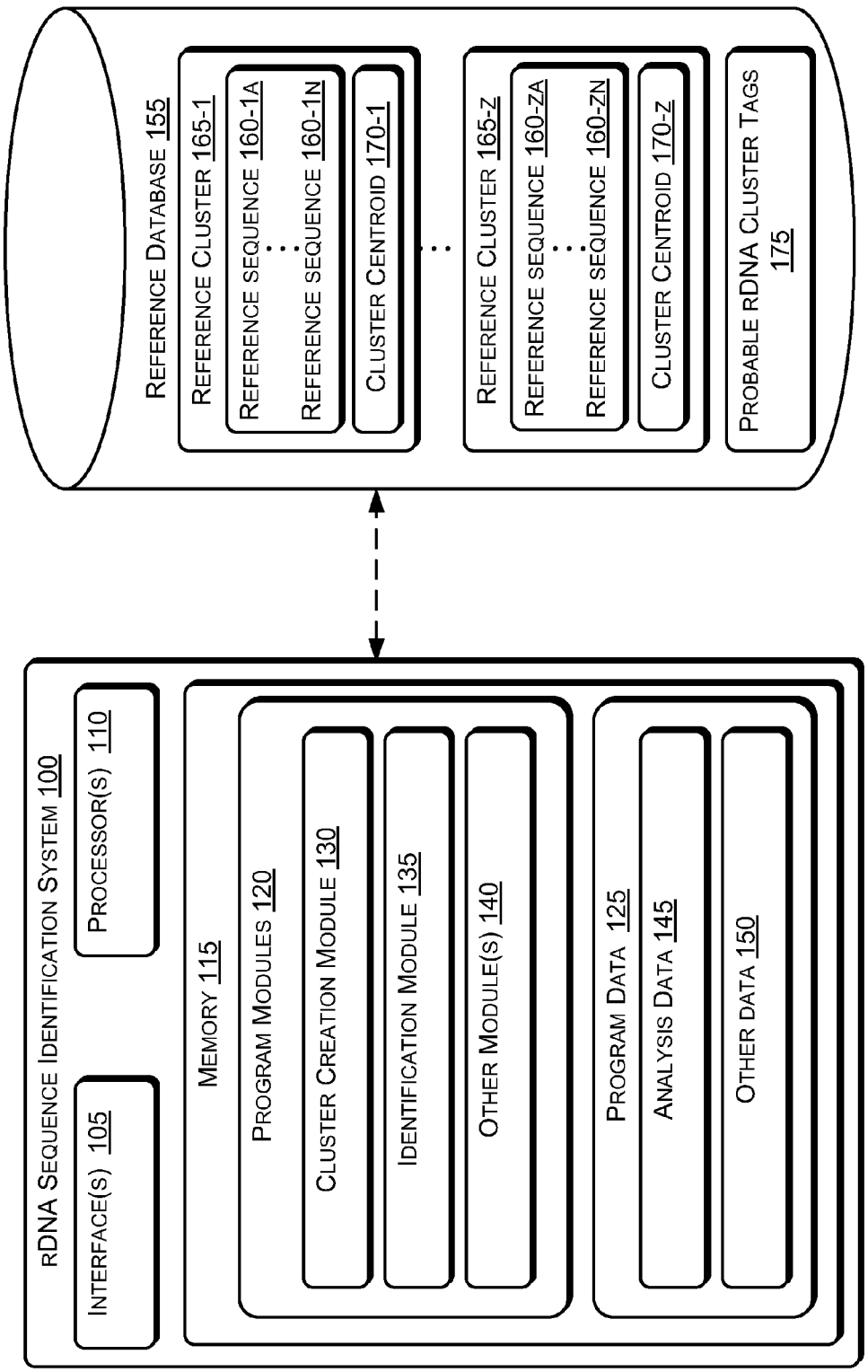
FIG. 1 illustrates an exemplary system for identification of ribosomal deoxyribonucleic acid (rDNA) sequences from a sample containing unknown deoxyribonucleic acid DNA sequences, in accordance with an embodiment of the present subject matter.

Method(s) and a system(s) to identify a query sequence, from a sample containing unknown Deoxyribonucleic acid (DNA) sequences, as a ribosomal DNA (rDNA) sequence are described herein. The rDNA sequence can be identified as a partial or complete rDNA sequence. The rDNA sequence includes sequences derived from, for example, 5S rDNA, 16S rDNA, 23S rDNA, 5.8S rDNA, 18S rDNA and 28S rDNA.

In one implementation, the identification of the query sequence as an rDNA sequence is performed with respect to a reference database having a plurality of reference clusters, which are created by classifying a plurality of reference sequences. The reference sequences may be grouped into corresponding reference clusters based on one or more compositional characteristics of the plurality of reference sequences. In one implementation, the reference sequences may be clustered based on compositional characteristics, such as oligonucleotide frequency. The oligonucleotide frequency may be defined as the number of occurrences of all possible oligonucleotides of a given length in the query sequence.

Alternatively, other compositional characteristics, for example, guanine-cytosine (GC) content, which is the percentage of nucleobases in a query sequence that are either guanine or cytosine, may also be used for clustering the reference sequences.

Further, one or more probable rDNA clusters may be identified from the plurality of reference clusters based on an rDNA analysis. For the purposes of explanation, the probable rDNA clusters may be understood as those reference clusters in which rDNA fragments, i.e. genome fragments encompassing partial or complete portions rDNA sequences, such as 16S rDNA, 23S rDNA, 18S rDNA, and 28S rDNA sequences, occur in high frequency. In one implementation, rDNA analysis can include identifying and pre-tagging a set of reference clusters as the probable rDNA clusters. For the purpose, reference vectors corresponding to a plurality of reference rDNA sequences are generated. Subsequently, the frequency of hits of each of the reference clusters with respect to the reference rDNA sequences is computed. The hits are identified based on the distance between each of the rDNA vectors and cluster centroids corresponding to each of the reference clusters. A reference cluster is then tagged as a 'probable rDNA cluster' if the frequency of hits for that reference cluster, with respect to the reference rDNA sequences, exceeds a predetermined threshold.

In order to identify a query sequence as an rDNA sequence, one or more target clusters, from the reference clusters, corresponding to the query sequence may be selected based on a composition based analysis. In one implementation, the selection of the target clusters is based on distance, such as non-Euclidean distance, between the vector corresponding to the query sequence and the cluster centroids of each of the reference clusters. In another implementation, the composition based analysis computes a distance between a query vector corresponding to the query sequence and the cluster centroids of each of the reference clusters. Accordingly, one or more target cluster is selected based on the computed distances.

Subsequent to the selection of the target clusters, the proportion of target clusters which are pre-tagged as the probable rDNA clusters, is computed. In one implementation, this computed proportion may be compared with a predetermined threshold, and if the computed proportion exceeds the predetermined threshold, the query sequence may be identified as an rDNA sequence.

Since present identification technique employs a reference database that is grouped into a plurality of clusters and the query sequence is identified as an rDNA sequence based on the distances between the query sequence and the reference clusters, followed by computation of the proportion of the probable rDNA clusters, the efficiency of the present identification technique, in terms of computational time, and sensitivity is considerably improved.

While aspects of described systems and methods for the identification of the rDNA sequences from a sample containing unknown DNA sequences can be implemented in any number of different computing systems, environments, and/or configurations, the embodiments are described in the context of the following exemplary system(s).

Exemplary Systems

FIG. 1 illustrates an exemplary rDNA sequence identification system 100, according to an implementation of the present subject matter. The rDNA sequence identification system 100 can be implemented in systems that include, but are not limited to, desktop computers, hand-held devices, multiprocessor systems, personal digital assistants (PDAs), laptops, network computers, minicomputers, mainframe computers, and the like. In one implementation, the rDNA sequence identification system 100 includes interface(s) 105, one or more processor(s) 110, and a memory 115 coupled to the processor(s) 110.

The interfaces 105 may include a variety of software and hardware interfaces, for example, interfaces for peripheral device(s), such as a keyboard, a mouse, an external memory, and a printer. Further, the interfaces 105 may enable the rDNA sequence identification system 100 to communicate with other computing systems, such as web servers and external databases. The interfaces 105 can facilitate multiple communications within a wide variety of networks and protocol types, including wired networks, for example local area network (LAN), cable, etc., and wireless networks such as Wireless LAN (WLAN), cellular, or satellite. For the purpose, the interfaces 105 may include one or more ports for connecting a number of computing systems to each other or to another server computer. In one implementation, a taxonomic classification server communicates with the reference database via the interfaces 105.

The processor 110 can be a single processing unit or a number of units, all of which could include multiple computing units. The processor 110 may be implemented as one or more microprocessors, microcomputers, microcontrollers, digital signal processors, central processing units, state machines, logic circuitries, and/or any devices that manipulate signals based on operational instructions. Among other capabilities, the processor 110 is configured to fetch and execute computer-readable instructions and data stored in the memory 115.

The memory 115 may include any computer-readable medium known in the art including, for example, volatile memory such as static random access memory (SRAM) and dynamic random access memory (DRAM), and/or non-volatile memory, such as read only memory (ROM), erasable programmable ROM, flash memories, hard disks, optical disks, and magnetic tapes.

The memory 115 includes program module(s) 120 and program data 125. The program modules 120, amongst other things, include routines, programs, objects, components, data structures, etc., which perform particular tasks or implement particular abstract data types. The program data 125 serves, amongst other things, as a repository for storing data processed, received and generated by one or more of the program modules 120. The program modules 120 further include, for example, a cluster creation module 130, an identification module 135, and other module(s) 140. The other modules 140 may include programs that supplement applications on the rDNA sequence identification system 100, for example, programs in the operating system. The program data 125 includes, for example, analysis data 145 and other data 150.

The other data 150 includes data generated as a result of the execution of one or more modules in the other modules 140.

The rDNA sequence identification system 100 may be associated with a reference database 155. The reference database 155 can either be external or internal to the rDNA sequence identification system 100. The reference database 155 includes a plurality of reference sequences 160-1A . . . 160-ZN, hereinafter referred to as reference sequence(s) 160. The reference sequences 160 can be classified into a plurality of reference clusters 165-1 . . . 165-Z, hereinafter referred to as reference cluster(s) 165. In one implementation, the cluster creation module 130 may categorize the reference sequences 160 into the reference clusters 165 based on the compositional characteristics of the reference sequences 160. Although, the clustering of the reference sequences 160 is explained in considerable details with reference to oligonucleotide frequency as a compositional characteristics; however it will be appreciated that the other compositional characteristics, for example, GC content or other compositional characteristics may also be used.

In an implementation, the reference sequences 160 may include completely sequenced genomes of prokaryotic organisms downloaded from a database, such as GenBank, National Center of Biotechnology Information (NCBI), etc. These genome sequences are split into fragments of predetermined length, for example 1000 base pairs (bp). Subsequent to splitting, each of the fragments is treated as a reference sequence 160. In one implementation, the cluster creation module 130 computes frequencies of all possible tetranucleotides in each of the reference sequences 160 and accordingly generates a reference vector corresponding to each of the reference sequences 160. The reference vectors may be stored as 256-dimensional vectors. Subsequently, reference sequences 160, based on the corresponding reference vectors, may be classified into the reference clusters 165 using conventional clustering techniques, such as k-means clustering technique that partitions n number of observations into k number of clusters in which each observation belongs to the cluster with the nearest mean.

In an implementation, for forming the reference clusters 165, the cluster creation module 130 selects a predetermined number of the reference clusters 165 and then randomly tags the reference clusters 165 with a plurality of cluster centroids 170-1 . . . 170-Z, hereinafter referred to as cluster centroid(s) 170. For each of the reference vectors, the cluster centroid 170 closest to the reference sequence 160 is determined and accordingly the reference sequence 160 is moved to the corresponding reference cluster 165.

The closest reference cluster 165 may be determined based on a distance between the reference vector and the cluster centroids 170. The distance, for example, may be a Euclidean metric or a non-Euclidean distance metric, such as Manhattan distance (L1 norm). Further, if the reference sequence 160 under consideration is moved to a reference cluster, the cluster centroids 170 are computed again. The cluster centroid 170 represents the mean value of the reference vectors corresponding to the reference sequences 160 present in the reference cluster 165. In one implementation, the process of forming the reference clusters 165 can be performed repeatedly till the reference clusters 165 become stable or some maximum number of iterations have been performed. In one implementation, the cluster centroids 170 may be tagged to the corresponding reference clusters 165.

The cluster creation module 130 may also identify one or more 'probable rDNA clusters' from amongst the reference clusters 165. For the purpose of identification of the probable rDNA clusters, a plurality of reference rDNA sequences may be downloaded from a database, such as the ribosomal database project (RDP) database. Further, for each of the rDNA sequence, an rDNA vector, indicative of oligonucleotide frequency, such as frequencies of all possible tetranucleotides is generated. The rDNA vector may be in the form of a 256 dimensional vector.

A distance, such as the Manhattan distance, between each of the rDNA vectors and each of the cluster centroids 170 is computed. In one implementation, the cluster creation module 130 may identify the reference clusters 165 that have the distance less than a threshold distance, for example, a distance less than or equal to 0.9 unit. A hit may be understood to have occurred when the distance between a reference cluster and an rDNA vector is less than the threshold distance. The frequency of hits of each of the reference cluster with respect to the rDNA vectors, and accordingly reference rDNA sequences, is determined based on the computed distances. Further, the frequency of hits may be compared with a predetermined frequency and the reference clusters with the frequency of hits in excess to the predetermined frequency may be tagged as the probable rDNA clusters.

In another implementation, instead of considering the threshold distance, for each of the rDNA sequences, a set of the closest reference clusters 165 having a cumulative sequence count of at least a threshold sequence count, for example 50000 sequences, may be identified as hits to the given rDNA sequence. Subsequently, a subset of the identified reference clusters 165 are tagged as probable rDNA clusters if the frequency of hits is in excess to the predetermined frequency.

For the purpose of explanation, and not as a limitation, to identify a set of the closest reference clusters a distance between each of the reference clusters 165 and the reference rDNA sequences is determined. Subsequently, the reference cluster with a minimum distance between its cluster centroid and an rDNA sequence is identified. If the identified reference cluster has a sequence count greater than or equal to the threshold sequence count, the identified reference cluster 165 is considered as the closest reference cluster 165. However, if the identified reference cluster 165 has a sequence count less than the threshold sequence count, the next closest reference cluster 165 is identified.

The next closest cluster 165 is the reference cluster 165 with second minimum distance between its cluster centroid 170 and the rDNA sequence. Further, if the cumulative sequence count of these two identified reference clusters 165 is of at least the threshold sequence count, the two reference clusters 165 are identified as a set of closest reference clusters 165. Otherwise, next closest reference cluster 165 is identified and the process is repeated until the cumulative sequence count, i.e., the cumulative count of all the reference sequences 160 in the set of the closest reference clusters 165, is greater than or equal to the threshold sequence count.

The process is repeated for each of the reference rDNA sequences and the set of closest reference clusters 165 is identified for each of the reference rDNA sequences. Subsequently, from these set of closest reference clusters, one or more closest reference clusters are identified, i.e., a sub-set of the closest reference clusters. The sub-set of closest reference clusters is identified based on the frequency of hits of the reference clusters 165 in the set of closest reference clusters 165. In said implementation, a hit may be considered to have occur if the reference cluster 165 is identified as the closest reference cluster 165 with respect to a given rDNA sequence. Further, the frequency of hits may be compared with a predetermined frequency and the reference clusters 165 with the frequency of hits in excess to the predetermined frequency may be tagged as the probable rDNA clusters.

The information pertaining to the reference clusters tagged as probable rDNA clusters may be stored in probable rDNA clusters tags 175. For example, the probable rDNA clusters tags 175 may include an index of all the reference clusters 165 that are identified as the probable rDNA clusters. Conversely, the reference clusters 165 not identified as probable rDNA clusters are not indexed in the probable rDNA cluster tags 175. The threshold distance, predetermined frequency, and threshold sequence count may be stored in the analysis data 145.

In another implementation, the reference database 155 may be a pre-configured database, which includes the reference sequences 160 grouped into reference clusters 165, based on one or more compositional characteristics of the reference sequences 160. Further, the reference clusters 165 that are probable rDNA clusters may be pre-tagged as probable rDNA clusters by way of the probable rDNA cluster tags 175.

In one implementation, the identification module 135 selects one or more target clusters, from the reference clusters 165 based on a composition based analysis. The selection of the target cluster is based on composition of the query sequence. To select the target clusters, the identification module 135 initially generates a query vector corresponding to the query sequence. The query vector may be generated based on one or more compositional characteristics, such as frequencies of all possible tetranucleotides in the query sequence. It will be understood that compositional characteristics used for generating the query vector would be similar to the compositional characteristics used for generating the reference vectors.

Subsequently, distances such as Euclidean distances or non-Euclidean distances like the Manhattan distance (L1 norm), between the query vector and each of the cluster centroids 170 can be evaluated. The identification module 135 then selects one or more of the reference clusters 165 as the target clusters corresponding to the query vector. In one implementation, the selection of target clusters for a query vector may be based on either a threshold distance (for example, 0.9) or a threshold cumulative sequence count (for example, 50000) of the closest reference clusters or both. In an example, one or more of the reference clusters 165 having a distance, from the query vector, less than the threshold distance may be selected as the target clusters. Further, the selection of the target clusters based on the threshold sequence count is similar to as described for identification of a set of the closest reference clusters 165. Additionally, the identification module 135 may determine the proportion of probable rDNA clusters from the target clusters. For the purpose, the target clusters, which are tagged as the probable rDNA clusters may be identified and accordingly the proportion of probable rDNA clusters from the target clusters may be computed.

The identification module 135 may be configured to compare the proportion of probable rDNA clusters with a predetermined proportion. Based on the comparison, the identification module 135 may identify the query sequence as an rDNA sequence, for example, when the proportion of probable rDNA clusters is in excess to the predetermined proportion, the query sequence may be identified as an rDNA sequence. In one implementation, the predetermined portion is $2/3^{rd}$ of the target clusters or in other words, 66% of the target clusters. In said implementation, the query sequence is identified as the rDNA sequence, if at least 66% of the target clusters are tagged as probable rDNA clusters.

The provision of having the reference database 155 including the reference sequences 160 classified into plurality of the reference clusters 165 and tagging a subset of these reference clusters 165 as the probable rDNA clusters provides for a reduction in computing time and resources.

Validation and Results

The present identification technique has been validated with reference to the reference database 155 including the reference clusters 165 with a subset of the reference clusters 165 tagged as the probable rDNA clusters. Subsequent to creation of the reference clusters 165 and tagging a subset of the created reference clusters 165 as probable rDNA clusters, the present identification technique, illustrated as embodiments of the present subject matter, is validated using query sequences of varying lengths. The present identification technique has been validated for identification of 16S rDNA sequences, 18S rDNA sequences, 23S rDNA sequences, and 28S rDNA sequences.

For the identification of probable 16S rDNA clusters, 63,325 16S rDNA sequences from fully sequenced prokaryotic genomes were obtained from the Ribosomal Database Project (RDP) database as accessible through the URL rdp.cme.msu.edu. The downloaded 16S rDNA sequences may be understood as the reference rDNA sequences. For every rDNA sequence, a rDNA vector representing the frequencies of all 256 tetranucleotides was generated. The Manhattan distance (L1 norm) of each vector to all pre-computed cluster centroids of the reference clusters 165, was obtained. The reference clusters 165 having the least distance with the rDNA vector and having a cumulative sequence count of 50000 fragments were identified. This process was repeated using rDNA vectors corresponding to each of the 63,325 16S rDNA sequences. The frequency with which each cluster is picked up by these sequences was calculated.

The reference clusters 165 having the frequency of hits greater than the predetermined frequency were identified and tagged as the probable 16S rDNA clusters. The predetermined frequency of hits was chosen as 10000 hits. Accordingly, a reference cluster, say, the reference cluster 165-1 was selected as a probable 16S rDNA cluster, if at least 10000 16S rDNA vectors (one-sixth of the total 16S rDNA sequences) have hits with that reference cluster 165-1.

For the purpose of identification of 16S rDNA sequences, query sequences of varying lengths were generated by randomly fragmenting 16S rDNA sequences (downloaded from the Ribosomal Database Project; rdp.cme.msu.edu) belonging to 1616 distinct genera. Based on the lengths of the query sequences, the query sequences were divided into four validation data sets, termed as 16S rDNA-Sanger data set, 16S rDNA-454:400 data set, 16S rDNA-454:250 data set, and 16S rDNA-454:100 data set. Each of these data sets contained 1,00,000 reads. Further, a query sequence was identified as a 16S rDNA sequence when at least 66% of the target clusters corresponding to the query sequence belonged to the pre-tagged set of 'probable 16S rDNA clusters'.

The query sequences constituting these four data sets simulated typical sequence lengths obtained from commonly used sequencing techniques. For example, query sequences constituting the 16S rDNA-Sanger data set, having sequence length centered around 800 base pairs, simulated reads or sequences obtained using Sanger sequencing technology; query sequences constituting 16S rDNA-454:400 data set, having sequence length centered around 400 base pairs, simulated reads or sequences obtained using 454-GS-FLX-Titanium sequencing technology; query sequences constituting the 16S rDNA-454:250 data set, having sequence length centered around 250 base pairs, simulated reads or sequences obtained using 454-GS-FLX-Standard sequencing technology, and 16S rDNA-454:100 data set, having sequence length centered around 100 base pairs, simulated reads or sequences obtained using Roche-454-GS20 sequencing technology.

The present identification technique was applied to these validation data sets and the percentage of the query sequences in each data set, which were classified by the technique as a 16S rDNA sequence, was recorded. Table 1 illustrates results of the validation of the present identification technique obtained with four validation data sets, namely, 16S rDNA-Sanger data set, 16S rDNA-454:400 data set, 16S rDNA-454:250 data set, and 16S rDNA-454:100 data set.

TABLE 1

| Validation Data Set | Length of Query Sequence (in base pairs) | % of query sequences correctly identified as 16S rDNA sequence |
|---|---|---|
| 16S rDNA-Sanger | 800 | 96.5 |
| 16S rDNA-454:400 | 400 | 96.2 |
| 16S rDNA-454:250 | 250 | 93 |
| 16S rDNA-454:100 | 100 | 90.7 |

As seen from Table 1, the present identification technique is able to detect 16S rDNA sequences from the 16S rDNA validation data sets with high sensitivity. It may also be observed, that the sensitivity of identifying 16S rDNA sequences by the present identification technique increases as the length of the query sequences increases.

In order to quantify the false positive rate of the present identification technique, four validation data sets were generated by randomly fragmenting 1000 completely sequenced genomes downloaded from the NCBI database. It was ensured that none of the fragments in the validation data sets contained 16S rDNA sequences. The validation data sets, mimicking those obtained using the same four sequencing technologies, were termed as non-16S rDNA-Sanger data set, non-16S rDNA-454:400 data set, non-16S-454:250 data set, non-16S-454:100 data set.

The non-16S rDNA query sequences in these validation data sets were also given as input, and the percentage of sequences in each data set, misclassified by the present identification technique as a probable 16S rDNA sequence was recorded. Table 2 illustrates validation of the present identification technique with respect to four validation data sets, namely, non-16S rDNA-Sanger data set, non-16S rDNA-454:400 data set, non-16S rDNA-454:250 data set, and non-16S rDNA-454:100 data set.

TABLE 2

| Validation Data Set | Length of Query Sequence (in base pairs) | % of query sequences wrongly identified as 16S rDNA sequence |
|---|---|---|
| Non-16S rDNA-Sanger | 800 | 4.5 |
| Non-16S rDNA-454:400 | 400 | 8 |
| Non-16S rDNA-454:250 | 250 | 8.2 |
| Non-16S rDNA-454:100 | 100 | 9.8 |

Table 2 depicts that the false positive rate is below 10% indicating a high specificity of the present identification technique. Further, it may also be observed that the number of false positives identified by the present identification technique also decreases with increasing lengths of the query sequences.

The results of present identification technique have also been validated using a "leave one clade out" strategy. In such as a strategy, identifying and pre-tagging probable 16S rDNA clusters is done using a modified set of 16S rDNA sequences. This modified set does not contain 16S rDNA sequences belonging to the removed clade. A clade may correspond to a genus or a family or an order or a class or a phylum. Subsequently, the query 16S rDNA sequences derived from the removed clade are analyzed using the re-computed set of tagged 'probable 16S rDNA clusters'. Such a strategy was intended to closely mimic sequences derived from a typical metagenomic scenario, where majority of sequences belong to hitherto unknown or new clades. For example, to mimic a new species scenario, the probable rDNA cluster tags 175 are re-computed using a modified set of 16S rDNA sequences, which do not include 16S rDNA sequences belonging to this species. Further, the query 16S rDNA sequences derived from this species were used for validating the new species scenario. Table 3 shows the performance of the present identification technique with the 16S rDNA sequences originating from new species, genus, family, order, class, and phylum respectively.

TABLE 3

| Source of the query sequence | % of sequences identified as 16S rDNA sequences Length of the query sequences | | | |
|---|---|---|---|---|
| | 800 bp | 400 bp | 250 bp | 100 bp |
| Known Species | 96.5 | 96.2 | 93 | 90.7 |
| New Species | 96.4 | 94.1 | 91.3 | 85.3 |
| New Genus | 94.5 | 91.3 | 85.3 | 71.2 |
| New Family | 93.5 | 90.2 | 84.1 | 70.6 |
| New Order | 92.3 | 90.1 | 84.8 | 70.6 |
| New Class | 91.0 | 90.0 | 83.8 | 70.0 |
| New Phylum | 89.2 | 88.4 | 82.4 | 69.5 |

Results illustrated in table 3 indicate that the present identification technique is able to detect 16S rDNA sequence from new organisms, belonging to even an entirely new phylum with greater than 80% sensitivity if the query sequence length is greater than 250 base pairs. Even with the weak composition signal obtained from the query sequences with length as low as 100 base pairs, the present identification technique is able to achieve a sensitivity of greater than 70%. Thus, the present identification technique can be used for detecting the 16S rDNA sequence in typical metagenomes, wherein majority of organisms belong to entirely new species, genus, family, order, class and phyla.

Similar to the process used for the identification of the 16S rDNA sequences, for the purpose of identification of probable 23S rDNA clusters 2700 23S rDNA sequences from fully sequenced prokaryotic genomes were obtained from the NCBI database. Likewise, for identification of probable 18S rDNA and 28S rDNA clusters, 7070 18S rDNA sequences and 2051 28S rDNA sequences from eukaryotic genomes were obtained from the NCBI database. As mentioned previously, the downloaded 23S rDNA sequences, 18S rDNA sequences, and 28S rDNA sequences, can be understood as the reference rDNA sequences. For every 23S rDNA, 18S rDNA, and 28S rDNA sequence, a corresponding rDNA vector representing the frequencies of all 256 tetranucleotides in the respective sequences were generated. The Manhattan distance (L1 norm) of each vector to all pre-computed cluster centroids of the reference clusters 165, was obtained. The reference clusters 165 having the least distance with the 23S rDNA, 18S rDNA, and 28S rDNA vectors respectively, and having a cumulative sequence count of 50000 fragments were identified.

This process was repeated using 23S rDNA, 18S rDNA, and 28S rDNA vectors corresponding to each of the 2700 23S rDNA sequences, 7070 18S rDNA, and 2051 28S rDNA sequences respectively. The frequency with which each cluster is picked up by these sequences was calculated. The reference clusters 165 having the frequency of hits greater than the predetermined frequency of hits were identified and tagged as the probable 23S rDNA, 18S rDNA and 28S rDNA clusters respectively. The predetermined frequency of hits was chosen as 450 hits for 23S rDNA, 1180 hits for 18S rDNA sequences, and 342 hits for 28S rDNA sequences. Accordingly, a reference cluster was selected as a probable 23S rDNA cluster, if at least 450 23S rDNA vectors (one-sixth of the total 23S rDNA sequences) have hits with that cluster. Likewise, a reference cluster was selected as a probable 18S rDNA cluster, if at least 1180 18S rDNA vectors (one-sixth of the total 18S rDNA sequences) have hits with that cluster and a reference cluster was selected as a probable 28S rDNA cluster, if at least 342 28S rDNA vectors (one-sixth of the total 28S rDNA sequences) have hits with that cluster.

Further, for the identification of 23S rDNA, query sequences of varying lengths were generated by randomly fragmenting 23S rDNA sequences belonging to 566 distinct genera. Similarly, for the identification of 18S rDNA, query sequences of varying lengths were generated by randomly fragmenting 18S rDNA sequences belonging to 2472 distinct genera; and for the identification of 28S rDNA, query sequences of varying lengths were generated by randomly fragmenting 28S rDNA sequences belonging to 517 distinct genera. The 23S rDNA, 18S rDNA, and 28S rDNA sequences, which were randomly fragmented, were downloaded from the NCBI database. Based on the lengths of the query sequences, the query sequences were divided into four validation data sets, termed as rDNA-Sanger data set, rDNA-454:400 data set, rDNA-454:250 data set, and rDNA-454:100 data set. For example, for 23S rDNA, the four validation data sets were 23S rDNA-Sanger data set, 23S rDNA-454:400 data set, 23S rDNA-454:250 data set, and 23S rDNA-454:100 data set. Similarly, for 18S rDNA the four validation data sets were 18S rDNA-Sanger data set, 18S rDNA-454:400 data set, 18S rDNA-454:250 data set, and 18S rDNA-454:100 data set; and for 28S rDNA the four validation data sets were 28S rDNA-Sanger data set, 28S rDNA-454:400 data set, 28S rDNA-454:250 data set, and 28S rDNA-454:100 data set. Each of these data sets contained 25,000 reads. The query sequences corresponding to 23S rDNA, 28S rDNA, and 18S rDNA constituting the four data sets simulated typical sequence lengths obtained from commonly used sequencing techniques, as explained previously with respect to 16S rDNA. Further, a query sequence was identified as a 23S rDNA, a 18S rDNA, or a 28S rDNA sequence when at least 66% of the target clusters corresponding to the query sequence belonged to the pre-tagged set of 'probable 23S rDNA clusters', 'probable 18S rDNA clusters', or 'probable 28S rDNA clusters', respectively.

The present identification technique was applied to these validation data sets and the percentage of query sequences in each data set, which were classified by the present identification technique as a 23S rDNA sequence, 18S rDNA sequence, and 28S rDNA sequence were recorded. Table 4a, 4b, and 4c illustrate results of the validation of the present identification technique obtained with four validation data sets for 23S rDNA sequence, 18 S rDNA sequence, and 28 rDNA sequence respectively.

As previously mentioned, Table 4a illustrates the results obtained with the four 23S rDNA validation data sets namely, 23S rDNA-Sanger data set, 23S rDNA-454:400 data set, 23S rDNA-454:250 data set, and 23S rDNA-454:100 data set.

TABLE 4a

| Validation Data Set | Length of Query Sequence (in base pairs) | % of query sequences correctly identified as 23S rDNA sequence |
| --- | --- | --- |
| 23S rDNA-Sanger | 800 | 99.3 |
| 23S rDNA-454:400 | 400 | 97.5 |
| 23S rDNA-454:250 | 250 | 91.8 |
| 23S rDNA-454:100 | 100 | 77.5 |

Similarly, Table 4b illustrates the results obtained with the four 18S rDNA validation data sets namely, 18S rDNA-Sanger data set, 18S rDNA-454:400 data set, 18S rDNA-454:250 data set, and 18S rDNA-454:100 data set.

TABLE 4b

| Validation Data Set | Length of Query Sequence (in base pairs) | % of query sequences correctly identified as 18S rDNA sequence |
| --- | --- | --- |
| 18S rDNA-Sanger | 800 | 87 |
| 18S rDNA-454:400 | 400 | 90.5 |
| 18S rDNA-454:250 | 250 | 87.5 |
| 18S rDNA-454:100 | 100 | 50.2 |

Similarly, Table 4c illustrates the results obtained with the four 28S rDNA validation data sets, namely, 28S rDNA-Sanger data set, 28S rDNA-454:400 data set, 28S rDNA-454:250 data set, and 28S rDNA-454:100 data set.

TABLE 4c

| Validation Data Set | Length of Query Sequence (in base pairs) | % of query sequences correctly identified as 28S rDNA sequence |
| --- | --- | --- |
| 28S rDNA-Sanger | 800 | 85.8 |
| 28S rDNA-454:400 | 400 | 86.5 |
| 28S rDNA-454:250 | 250 | 84.8 |
| 28S rDNA-454:100 | 100 | 59.3 |

As seen from Tables 4a, 4b, and 4c, the present identification technique is able to detect 23S rDNA, 18S rDNA, and 28S rDNA sequences from the corresponding validation data sets with high sensitivity. It may also be observed, that the sensitivity of identifying rDNA sequences by the present identification technique increases as the length of the query sequences increases.

As previously mentioned, in order to quantify the false positive rate of the present identification technique, four validation data sets corresponding to 23S rDNA (were generated by randomly fragmenting 1000 completely sequenced genomes downloaded from the NCBI database. Likewise, eight more validation data sets (four each for 18S rDNA and 28S rDNA respectively) were generated by randomly fragmenting 15 completely sequenced eukaryotic genomes downloaded from the NCBI database. Similar to validation results with respect to 16S rDNA, it was ensured that none of the fragments in the validation data sets contained 23S rDNA, 18S rDNA or 28S rDNA sequences respectively. The validation data sets, mimicking those obtained using the same four sequencing technologies, were termed as non-rDNA-Sanger data set, non-rDNA-454:400 data set, non-454-250 data set, non-454-100 data set. For example, for the 23S rDNA the four validation data sets were non-23 S rDNA-Sanger data set, non-23 S rDNA-454:400 data set, non-23S-454:250 data set, non-23S-454:100 data set. Similarly, for 18S rDNA the four validation data sets were non-18S rDNA-Sanger data set, non-18S rDNA-454:400 data set, non-18S rDNA-454:250 data set, and non-18S rDNA-454:100 data set; and for non-28S rDNA the four validation data sets were non-28S rDNA-Sanger data set, non-28S rDNA-454:400 data set, non-28S rDNA-454:250 data set, and non-28S rDNA-454:100 data set.

The non-23S rDNA, non-18S rDNA, and non-28S rDNA query sequences in the corresponding validation data sets were also given as input, and the percentage of sequences in each data set, misclassified by the present identification technique as a probable 23S rDNA, 18S rDNA, or 28S rDNA sequence respectively, was recorded. Table 5a, 5b, and 5c illustrates validation of the present identification technique with respect to four validation data sets for each of 23S rDNA sequences, 18S rDNA sequences, and 28S rDNA sequences respectively.

As previously mentioned, table 5a illustrates the results obtained with the four non-23S rDNA validation data sets namely, non-23S rDNA-Sanger data set, non-23S rDNA-454:400 data set, non-23S rDNA-454:250 data set, and non-23S rDNA-454:100 data set.

TABLE 5a

| Validation Data Set | Length of Query Sequence (in base pairs) | % of query sequences wrongly identified as 23S rDNA sequence |
|---|---|---|
| Non-23S rDNA-Sanger | 800 | 3.29 |
| Non-23S rDNA-454:400 | 400 | 8.64 |
| Non-23S rDNA-454:250 | 250 | 8.27 |
| Non-23S rDNA-454:100 | 100 | 14.6 |

Similarly, table 5b illustrates the results obtained with the four non-18S rDNA validation data sets namely, non-18S rDNA-Sanger data set, non-18S rDNA-454:400 data set, non-18S rDNA-454:250 data set, and non-18S rDNA-454:100 data set.

TABLE 5b

| Validation Data Set | Length of Query Sequence (in base pairs) | % of query sequences wrongly identified as 18S rDNA sequence |
|---|---|---|
| Non-18S rDNA-Sanger | 800 | 16.7 |
| Non-18S rDNA-454:400 | 400 | 12.4 |
| Non-18S rDNA-454:250 | 250 | 22.9 |
| Non-18S rDNA-454:100 | 100 | 24 |

Likewise, table 5c illustrates the results obtained with the four non-28S rDNA validation data sets namely, non-28S rDNA-Sanger data set, non-28S rDNA-454:400 data set, non-28S rDNA-454:250 data set, and non-28S rDNA-454:100 data set.

TABLE 5c

| Validation Data Set | Length of Query Sequence (in base pairs) | % of query sequences wrongly identified as 28S rDNA sequence |
|---|---|---|
| Non-28S rDNA-Sanger | 800 | 16.5 |
| Non-28S rDNA-454:400 | 400 | 16.6 |
| Non-28S rDNA-454:250 | 250 | 18.5 |
| Non-28S rDNA-454:100 | 100 | 18.9 |

Table 5a depicts that the false positive rate is below 15%, table 5b depicts that the false positive rate is below 24%, and table 5c depicts that the false positive rate is below 19%, indicating the high accuracy of the present identification technique. As it was observed for 16S rDNA data sets, the number of false positives identified by the present identification technique for 23S rDNA, 18S rDNA, and 28S rDNA data sets also decreases with increasing length of the query sequence.

The results of present identification technique for identification of 23S rDNA, 18S rDNA, and 28S rDNA have also been validated using the "leave one clade out" strategy, as explained previously. Table 6a, 6b, and 6c show the performance of the present identification technique with 23S rDNA, 18S rDNA, and 28S rDNA sequences originating from new species, genus, family, order, class, and phylum respectively.

TABLE 6a

| Source of the query sequence | % of sequences identified as 23S rDNA sequences Length of the query sequences | | | |
|---|---|---|---|---|
| | 800 bp | 400 bp | 250 bp | 100 bp |
| Known Species | 99.9 | 97.5 | 91.8 | 86.2 |
| New Species | 94.9 | 83.4 | 76.5 | 70.7 |
| New Genus | 93.3 | 83.2 | 75.7 | 65.2 |
| New Family | 93.1 | 82.3 | 75.4 | 64.8 |
| New Order | 93.1 | 82.3 | 75.2 | 64.7 |
| New Class | 92.9 | 82.0 | 75.2 | 64.7 |
| New Phylum | 92.5 | 82.0 | 74.6 | 64 |

Results illustrated in table 6a indicate that the present identification technique is able to detect 23S rDNA sequence from new organisms, belonging to even an entirely new phylum with greater than 80% sensitivity if the query sequence length is greater than 250 base pairs. Even with the weak composition signal obtained from the query sequences with length as low as 100 base pairs, the present identification technique is able to achieve a sensitivity of greater than about 65%.

TABLE 6b

| Source of the query sequence | % of sequences identified as 18S rDNA sequences Length of query sequences | | | |
|---|---|---|---|---|
| | 800 bp | 400 bp | 250 bp | 100 bp |
| Known Species | 87 | 90.5 | 87.5 | 50.2 |
| New Species | 84.3 | 86.5 | 72.6 | 46.2 |
| New Genus | 82.8 | 74.9 | 53.6 | 40.3 |
| New Family | 82.7 | 74.8 | 53.4 | 36.9 |
| New Order | 82.7 | 74.6 | 53.4 | 35.2 |
| New Class | 82.2 | 73.1 | 53.3 | 30.1 |
| New Phylum | 81.1 | 72.6 | 52.5 | 29 |

Results illustrated in table 6b indicate that the present identification technique is able to detect 18S rDNA sequence from new organisms, belonging to even an entirely new phylum with greater than 72% sensitivity if the query sequence length is greater than 400 base pairs.

TABLE 6c

| Source of the query sequence | % of sequences identified as 28S rDNA sequences Length of query sequences | | | |
|---|---|---|---|---|
| | 800 bp | 400 bp | 250 bp | 100 bp |
| Known Species | 85.8 | 86.5 | 84.8 | 59.2 |
| New species | 80.3 | 84.3 | 80.2 | 55.2 |
| New Genus | 74.2 | 74.1 | 73.1 | 46.3 |
| New Family | 73.5 | 72.3 | 55.8 | 42.1 |

TABLE 6c-continued

| Source of the query | % of sequences identified as 28S rDNA sequences Length of query sequences | | | |
|---|---|---|---|---|
| sequence | 800 bp | 400 bp | 250 bp | 100 bp |
| New Order | 64.6 | 69.7 | 54.4 | 40.1 |
| New Class | 61.2 | 66.9 | 54.1 | 37.4 |
| New Phylum | 57.5 | 66.8 | 50.2 | 37 |

Results illustrated in table 6c indicate that the present identification technique is able to detect 28S rDNA sequence from new organisms, belonging to even an entirely new phylum with greater than 66% sensitivity if the query sequence length is greater than 400 base pairs.

Thus, the present identification technique can be used for detecting 23S rDNA, 18S rDNA, 28S rDNA sequences in typical metagenomes, wherein majority of organisms belong to entirely new species, genus, family, order, class and phyla.

Table 7 shows that the present identification technique achieves approximately 233 fold reduction in the computational time over conventional technique, rna-hmm algorithm (Ying Huang et al., 2009). These time estimates were obtained using a desktop computer with 2.33 GHz central processing unit (CPU) with 2 GB random access memory (RAM).

TABLE 7

| Technique | Time taken (in minutes) for analyzing 1 million 16S rDNA/ 23S rDNA query sequences |
|---|---|
| Present Identification Technique | 54 |
| rna-hmm (Ying Huang et al, 2009) | 12400 |

Thus, it can be observed from table 7 that the present identification technique can process a million sequences in less than an hour as compared to more than 8 days taken by hmm-fs program (Ying Huang et al., 2009). In addition, the high sensitivity values obtained with the present identification technique using exhaustive validation sets at all taxonomic levels, as illustrated in Table 1, 2, and 3, indicate that this technique can be applied to any metagenomic data set for facilitating quick estimation of taxonomic diversity. Since the current in-silico identification technique is able to detect 16S rDNA, 23S rDNA, 18S rDNA and 28S rDNA sequences from fragments of genomic DNA of various lengths with high sensitivity and faster speed, the entire experimental step of primer based rDNA amplification, cloning and sequencing can be bypassed thereby saving a considerable amount of time, efforts, and resources.

Figure 2:
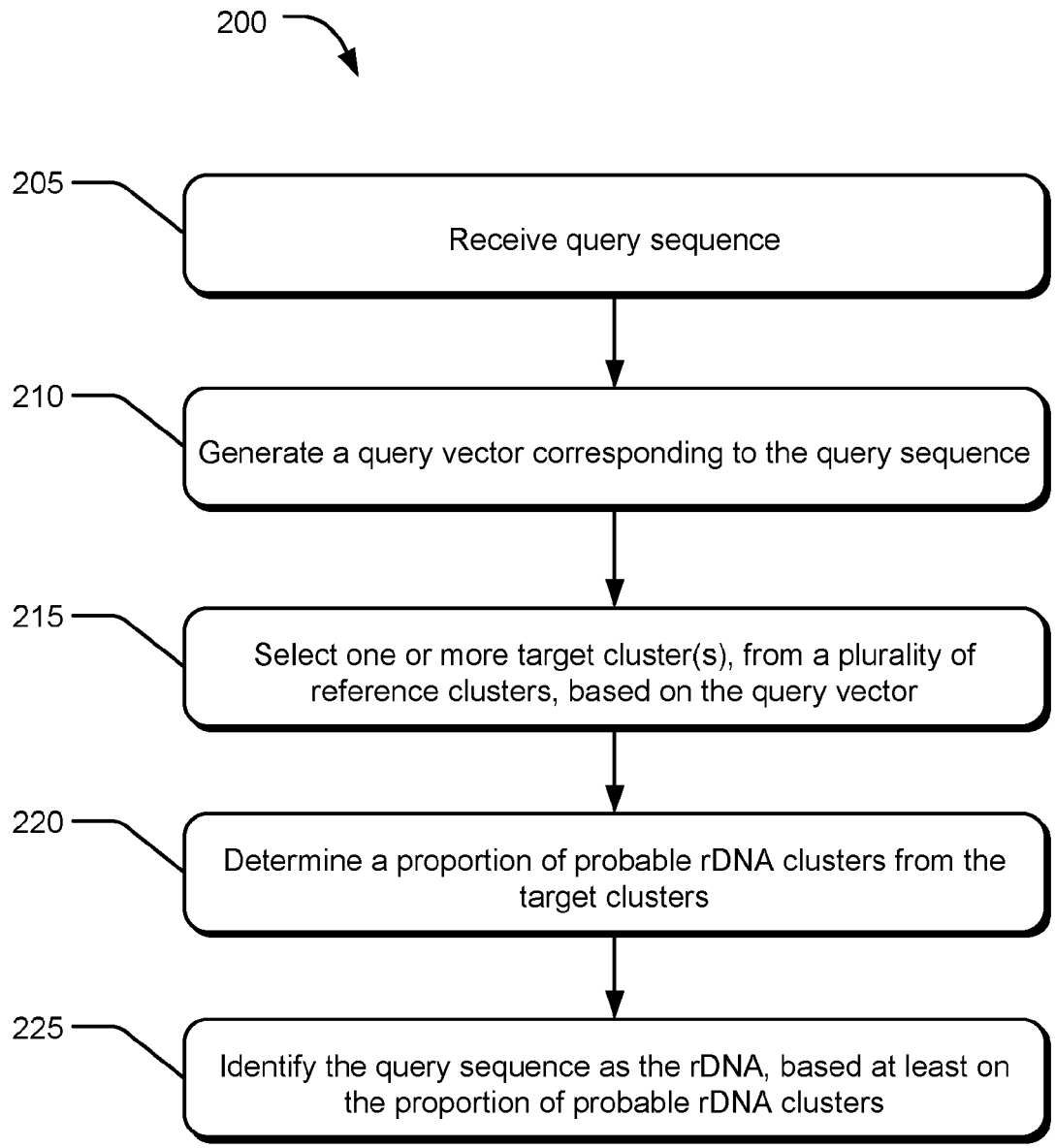
FIG. 2 illustrates an exemplary method for identification of rDNA sequences from a sample containing unknown DNA sequences, in accordance with an implementation of the present subject matter.
Figure 3:
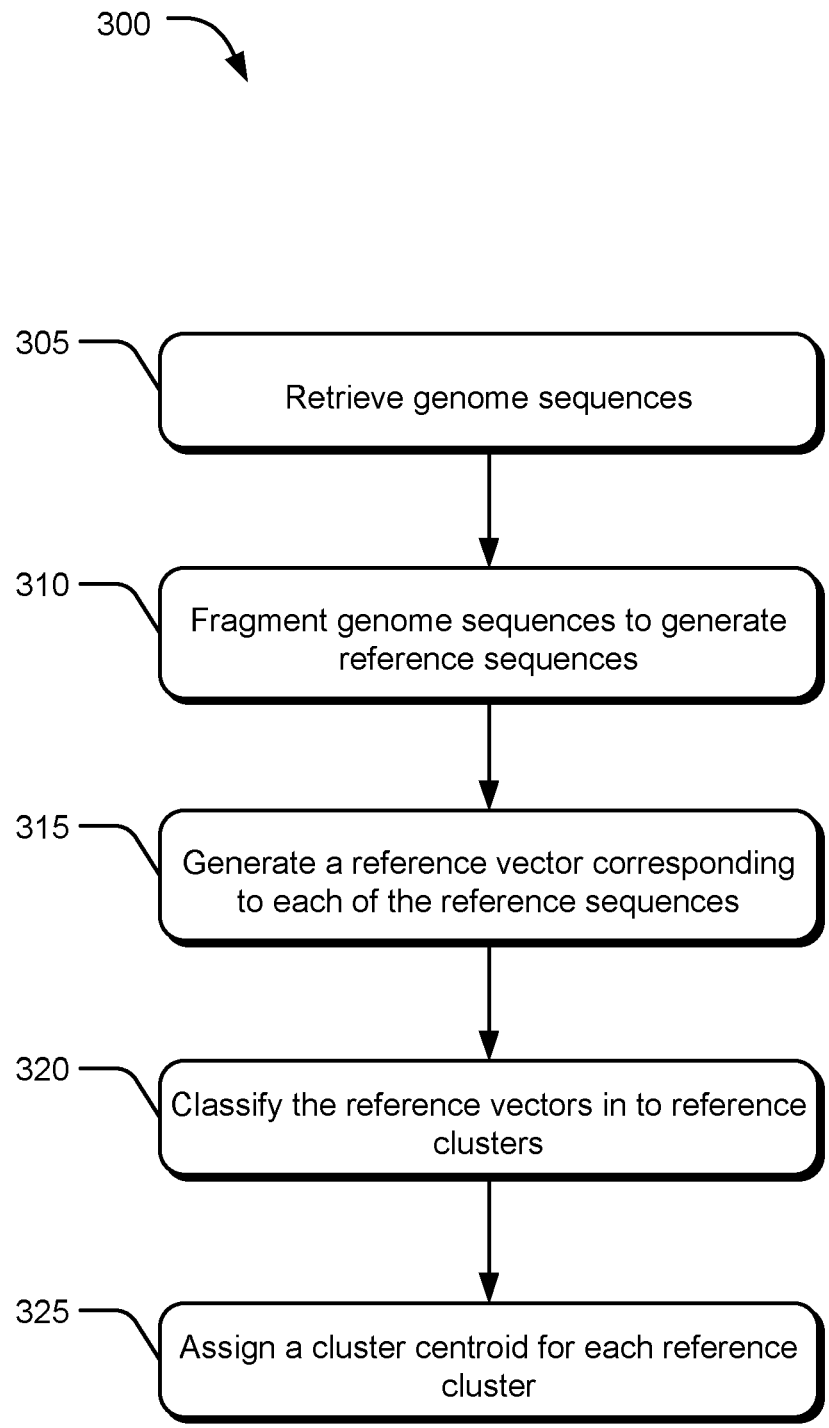
FIG. 3 illustrates an exemplary method to classify reference sequences into reference clusters, in accordance with an implementation of the present subject matter.
Figure 4:
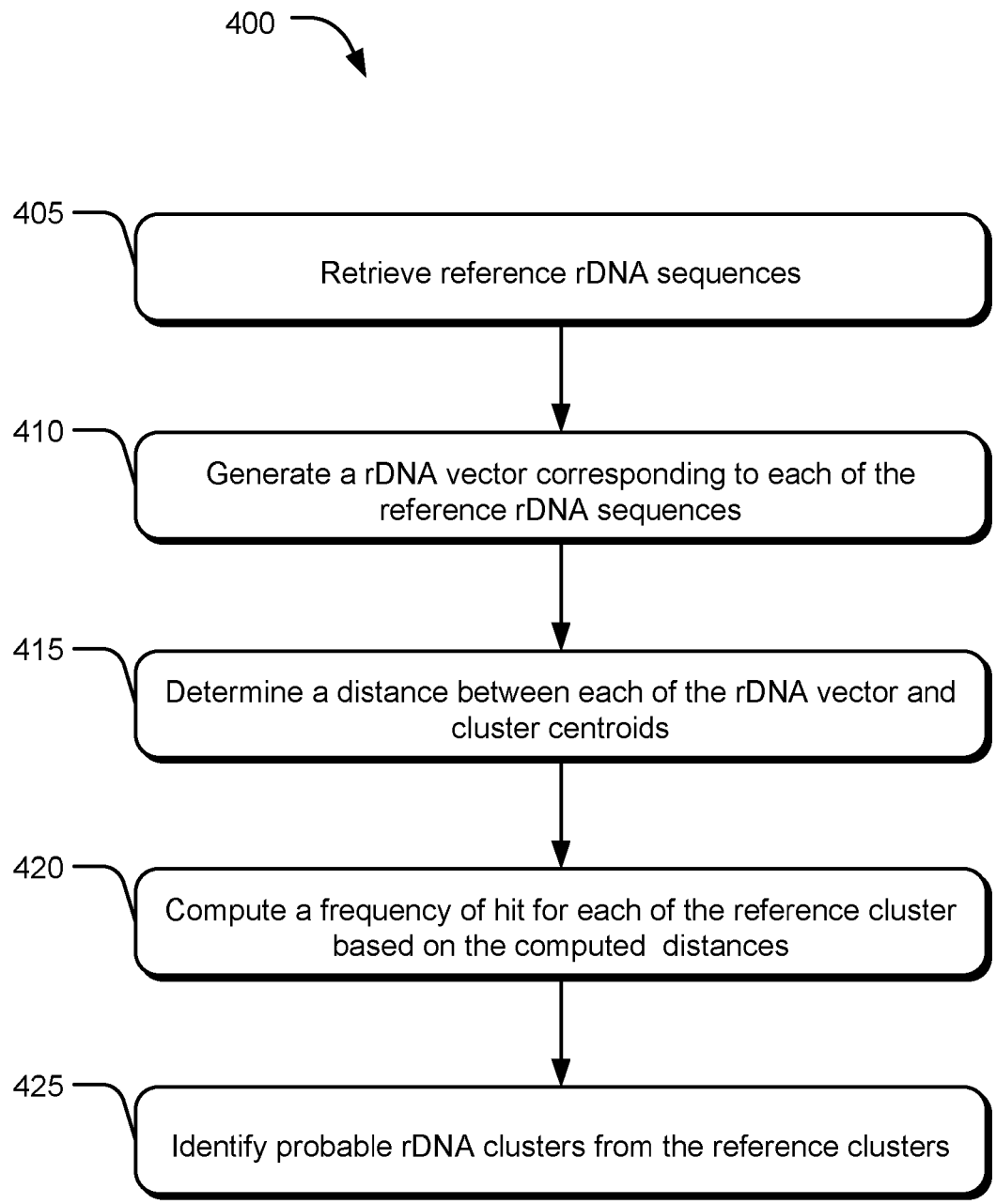
FIG. 4 illustrates an exemplary method to identify probable rDNA clusters from amongst reference clusters in a reference database, in accordance with an implementation of the present subject matter.

FIG. 2 illustrates an exemplary method 200 for identification of rDNA sequences from a sample containing unknown DNA sequences, FIG. 3 illustrates an exemplary method 300 for classification of reference sequences into reference clusters, in accordance with an implementation of the present subject matter, and FIG. 4 illustrates an exemplary method 400 for identifying probable rDNA clusters from reference clusters in a reference database, in accordance with an implementation of the present subject matter.

The exemplary methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

The order in which the methods are described is not intended to be construed as a limitation, and any number of the described method blocks can be combined in any order to implement the method, or an alternative method. Additionally, individual blocks may be deleted from the methods without departing from the spirit and scope of the subject matter described herein. Furthermore, the methods can be implemented in any suitable hardware, software, firmware, or combination thereof. The method is presently provided for a query sequence. It would be appreciated that the same method can also be implemented for a plurality of query sequences without deviating from the scope of the present subject matter.

At block 205, a query sequence from a sample containing unknown DNA sequences, such as a metagenome, may be received. For example, the query sequence from a metagenome can be received by an identification module, such as identification module 135. The query sequence may be in the form of a nucleic acid sequence.

At block 210, a query vector corresponding to the query sequence is generated, based on a composition based analysis of the query sequence. For example, the identification module 135 on receiving the query sequence performs a composition based analysis to generate the query vector. The composition based analysis is performed based on compositional characteristics, such as oligonucleotide frequencies and GC content of the query sequence.

At block 215, one or more target clusters are identified, based on the query vector, from the plurality of reference clusters. For example, the identification module 135 may identify one or more target clusters from the plurality of reference clusters 165 in the reference database 155. In one implementation, the reference database 155 may be a pre-configured database having the pre-configured reference clusters 165. Alternately, the reference sequences may be classified into the reference clusters 165 using a cluster creation module 130, as will be explained in detail with reference to description of FIG. 3.

In an implementation, one or more target clusters may be identified based on the composition-based analysis of the query sequence. For example, a non-Euclidean distance metrics, such as Manhattan distance (L1 norm), may be computed between the query vector and the respective cluster centroid 170 associated with each of the reference clusters 165 in the reference database. Based on the computed non-Euclidean distances the target clusters may be selected. In one example, the reference clusters 165 at non-Euclidean distance less than a predetermined distance may be selected as the target clusters. In another example, the reference clusters 165 being closest to the query sequence and having a cumulative sequence count greater than or equal to the threshold sequence count are tagged as the target clusters.

At block 220, the proportion of probable rDNA clusters from the target clusters may be determined. For example, the identification module 135 may determine the proportion of probable rDNA clusters from the target clusters. For this purpose, target clusters, which are tagged as the probable rDNA clusters may be identified and accordingly the proportion of probable rDNA clusters from the target clusters may be determined. In one implementation, the predetermined distance may be stored in analysis data, such as the analysis data 145.

At block 225, the query sequence is identified as the rDNA sequence, based on the proportion of target clusters, which belong to the pre-tagged set of probable rDNA clusters. For example, the identification module 135 compares the proportion of the identified probable rDNA clusters with a predetermined proportion and based on the comparison identifies the query sequence as the rDNA sequence. In one implementation, the query sequence is identified as the rDNA sequence, if the proportion of the probable rDNA clusters exceeds the predetermined proportion. Further, the predetermined proportion may be stored in the analysis data, such as the analysis data 145.

Since, the present identification technique is able to identify rDNA sequences from a sample containing unknown DNA sequences with high sensitivity and low computational time, the present identification technique, which is an in-silico technique, may be used to bypass the experimental step of primer based amplification, cloning and sequencing of the rDNA sequences, such as, 16S rDNA sequences, 23S rDNA sequences, 18S rDNA sequences and 28S rDNA sequences. Thus, the present identification technique saves a considerable amount of time, efforts, and resources.

Referring to FIG. 3, the method 300 classifies a plurality of reference sequences, such as the reference sequences 160, into a plurality of reference clusters, such as the reference clusters 165, according to an implementation of the present subject matter. The reference sequences 160 may be classified using a cluster creation module, such as the cluster creation module 130 of the rDNA sequence identification system 100.

At block 305, genome sequences may be retrieved and saved in a reference database, such as the reference database 155. In one implementation, the genome sequences may be retrieved in the form of completely sequenced prokaryotic genomes. For example, the rDNA sequence identification system 100 may communicate with an external database, such as GenBank or NCBI, and retrieve the reference sequences in the form of completely sequenced prokaryotic genomes from this external database. The genome sequences may be retrieved in the form of nucleic acid sequences corresponding to the genomes of completely sequenced prokaryotic organisms. Further, the reference database may contain reference sequences corresponding to the genomes of completely sequenced prokaryotic organisms or to the genomes corresponding to eukaryotic organisms or both.

At block 310, the genome sequences are be split into fragments of a predetermined length, for example, fragments with lengths of 1000 base pairs. Further, each of the fragment sequence may be considered as a reference sequence.

At block 315, a reference vector corresponding to each of the reference sequences may be generated. The reference vectors may be generated based on one or more compositional characteristics of the reference sequences. For example, the reference vectors may be generated based on frequencies of all possible oligonucleotides of a chosen length in the reference sequence.

At block 320 the reference sequences may be classified into the reference clusters using a clustering technique, such as k-means clustering technique, based on the reference vectors. In one implementation, the reference sequences with similar nucleotide composition may be classified together in one reference cluster.

At block 325, a cluster centroid may be assigned to each of the reference clusters. The cluster centroid may be computed based on the reference sequences, which are in that cluster. For example, the cluster centroid may be computed as the mean value of the reference vectors corresponding to the reference sequences included in a particular reference cluster.

Referring to FIG. 4, the method 400 identifies a plurality of probable rDNA clusters, from a plurality of reference clusters, such as the reference clusters 165, according to an implementation of the present subject matter. The probable rDNA clusters may be identified and tagged using a cluster creation module, such as the cluster creation module 130 of the rDNA sequence identification system 100.

At block 405, reference rDNA sequences may be retrieved from a database, such as the RDP database. In one implementation, the cluster creation module 130 may store these rDNA sequences in the analysis data 145.

At block 410, an rDNA vector corresponding to each of the reference rDNA sequences may be generated. The rDNA vectors may be generated based on one or more compositional characteristics of the reference sequences. For example, the rDNA vectors may be generated based on frequencies of all possible oligonucleotides of chosen length in the reference sequence.

At block 415, a distance, such as Manhattan distance, between each of the rDNA vectors and a cluster centroid of each of the reference clusters may be determined. In one implementation, each of the reference clusters 165 may be tagged with the cluster centroid 170 as explained in description of FIG. 3.

At block 420, a frequency of hit for each of the reference cluster may be computed based on the distances between the rDNA vectors and the cluster centroids corresponding to each of the reference clusters. In one implementation, the cluster creation module 130 may compare the distances of each of the reference clusters 165, from the rDNA vectors, with a threshold distance. Thus, a hit may be understood to have occurred when the distance between a reference cluster and an rDNA vector is less than the threshold distance, such as 0.9. Further, the frequency of hits of each of the reference cluster with respect to the rDNA vectors, and accordingly reference rDNA sequences, may be determined based on the computed non-Euclidean distances. In another implementation, for each rDNA sequence, a set of the closest reference clusters 165 having a cumulative sequence count of at least a threshold sequence count, for example 50000 sequences, may be identified as hits to the given rDNA sequence. In said implementation, a hit may be considered to have occurred if the reference cluster 165 is identified as the closest reference cluster 165 with respect to the given rDNA sequence. The threshold distance, the threshold sequence count, and the distances determined at the block 415 may be stored in the analysis data 145.

At block 425, the probable rDNA clusters from the reference clusters may be identified based on the frequency of hits. In one implementation, the frequency of hits may be compared with a predetermined frequency and the reference clusters 165 with the frequency of hits in excess to the predetermined frequency may be identified and tagged as the probable rDNA clusters. In another implementation, a set of the reference clusters 165 having a cumulative sequence count greater than a threshold sequence count, for example greater than 50000 sequences and each of the reference clusters 165 in the set having the frequency of hits in excess to the predetermined frequency may be tagged as the probable rDNA clusters.

Although embodiments for identification of rDNA sequences from a sample containing unknown DNA sequences have been described in language specific to structural features and/or methods, it is understood that the invention is not necessarily limited to the specific features or methods described. Rather, the specific features and methods are disclosed as exemplary embodiments for identification of rDNA sequences from the sample containing unknown DNA sequences.

We claim:

1. A computer implemented method for pre-tagging a subset of reference clusters from amongst a plurality of reference clusters as probable rDNA clusters and using information obtained by pre-tagging for identification of ribosomal deoxyribonucleic acid (rDNA) sequences from a sample containing a plurality of unknown DNA sequences, the method comprising:
   obtaining a plurality of reference sequences from a reference database;
   creating said plurality of reference clusters using said plurality of reference sequences;
   performing a rDNA analysis to pre-tag said subset of reference clusters, from amongst the plurality of reference clusters, as the probable rDNA clusters, wherein the rDNA analysis comprises:
      obtaining a plurality of the reference rDNA sequences from the reference database;
      generating a plurality of rDNA vectors corresponding to a plurality of reference rDNA sequences;
      computing a frequency of hits of each of said plurality of reference clusters corresponding to said plurality of reference rDNA sequences, wherein the frequency of hits is computed based on at least one of a threshold distance and a threshold sequence count;
      comparing for each of the plurality of reference clusters, the computed frequency of hits with a predetermined frequency;
      pre-tagging the subset of reference clusters from said plurality of reference clusters as the probable rDNA clusters, when the computed frequency of hits exceeds the predetermined frequency; and
   identifying a plurality of ribosomal deoxyribonucleic acid (rDNA) sequences from a sample containing a plurality of unknown DNA sequences based on the information obtained from pre-tagging, wherein the identifying includes:
      creating a plurality of query sequences corresponding to said plurality of unknown DNA sequences by sequencing genetic material obtained from the sample;
      computing a distance between a query vector corresponding to each query sequence and a cluster centroid of each of the plurality of reference clusters, wherein each of the plurality of reference clusters include said plurality of reference sequences, and wherein said plurality of reference sequences with similar composition are classified into at least one reference cluster;
      selecting one or more target clusters corresponding to the query sequence from the plurality of reference clusters, wherein the one or more target clusters are selected based on,
         a comparison of the distance of each of the plurality of reference clusters with the threshold distance; and
         a comparison of a cumulative sequence count of said plurality of reference clusters with the threshold sequence count;
      computing the proportion of pre-tagged probable rDNA clusters within the one or more target clusters, and
      identifying the query sequence as a rDNA sequence, when the computed proportion of the pre-tagged probable rDNA clusters exceeds a predetermined proportion.

2. The computer implemented method as claimed in claim 1 further comprising classifying said plurality of reference sequences, into the plurality of reference clusters, based on similarity in at least one compositional characteristic of the plurality of reference sequences.

3. The computer implemented method as claimed in claim 2, wherein the at least one compositional characteristic is one of an oligonucleotide frequency and a guanine-cytosine (GC) content.

4. The computer implemented method as claimed in claim 1, wherein computing the proportion of pre-tagged probable rDNA clusters comprises:
   identifying a number of target clusters pre-tagged as probable rDNA clusters; and
   comparing the number of the one or more identified target clusters pre-tagged as the probable rDNA clusters with the number of target clusters.

5. The computer implemented method as claimed in claim 1, wherein the rDNA sequence is at least one of a 5S rDNA, a 16S rDNA, a 23S rDNA, a 5.8S rDNA, a 18S rDNA, and a 28S rDNA sequence.

6. The computer implemented method as claimed in claim 1, wherein the query sequence has a length of one of 800 base pairs, 400 base pairs, 250 base pairs, and 100 base pairs.

7. The computer implemented method as claimed in claim 1, wherein the selecting further comprises:
   comparing the distance between the query vector and the cluster centroid of each of the plurality of reference clusters with the threshold distance; and
   selecting a reference cluster as a target cluster, when the distance between the query vector and the cluster centroid is greater than the threshold distance.

8. The computer implemented method as claimed in claim 1, wherein the selecting further comprises:
   identifying a reference cluster at a minimum distance from the query vector, based on computed distances, the one or more reference clusters comprising the identified reference cluster;
   determining a sequence count of the identified reference cluster; and
   comparing the sequence count with the threshold sequence count;
   select the identified reference cluster as target cluster, when the sequence count is greater than or equal to the threshold sequence count;
   iteratively identifying one or more next closest reference clusters, based on the computed distances, wherein the one or more reference clusters comprise the identified reference cluster and the one or more next closest reference clusters, and wherein the one or more next closest reference clusters are identified till a cumulative sequence count of the one or more reference clusters is greater than or equal to the threshold sequence count; and
   selecting the one or more reference clusters as the target clusters, when the cumulative sequence count is greater than or equal to the threshold sequence count.

9. A computer implemented system for pre-tagging a subset of reference clusters from amongst a plurality of reference clusters as probable rDNA clusters and using information obtained from pre-tagging for identification of ribosomal deoxyribonucleic acid (rDNA) sequences from a sample containing a plurality of unknown DNA sequences, the system comprising:
    a processor; and
    a memory coupled to the processor, wherein the processor is capable of executing the plurality of modules stored in the memory, said processor configured to,
        obtain a plurality of reference sequences from a reference database using a cluster creation module;
        create said plurality of reference clusters using said plurality of reference sequences;
        perform a rDNA analysis to pre-tag said subset of reference clusters from amongst the plurality of reference clusters as said probable rDNA clusters;
        obtain a plurality of reference rDNA sequences from the reference database based on said rDNA analysis;
        generate a plurality of rDNA vectors corresponding to a plurality of reference rDNA sequences, based on said rDNA analysis;
        compute a frequency of hits of each of said plurality of reference clusters corresponding to said plurality of reference rDNA sequences, wherein the frequency of hits is computed based on at least one of a threshold distance and a threshold sequence count;
        compare for each of the plurality of reference clusters, the computed frequency of hits with a predetermined frequency;
        pre-tag said plurality of reference clusters from said plurality of reference clusters as the probable rDNA clusters, when the computed frequency of hits exceeds the predetermined frequency;
    and said processor further configured to:
        identify a plurality of ribosomal deoxyribonucleic acid (rDNA) sequences from a sample containing a plurality of unknown DNA sequences based on the information obtained from pre-tagging;
        create a plurality of query sequences corresponding to said plurality of unknown sequences by sequencing genetic material obtained from the sample;
        compute a distance between a query vector corresponding to each query sequence and a cluster centroid of each of a plurality of reference clusters, wherein each of the plurality of reference clusters include said plurality of reference sequences, and wherein said plurality of reference sequences with similar composition are classified into at least one reference cluster;
        select one or more target clusters corresponding to the query sequence from the plurality of reference clusters, wherein the one or more target clusters are selected based on,
            a comparison of the distance of each of the plurality of reference clusters with the threshold distance; and
            a comparison of a cumulative sequence count of the plurality of reference clusters with the threshold sequence count;
        compute the proportion of the pre-tagged probable rDNA clusters within the one or more target clusters; and
        identify the query sequence as a rDNA sequence, when the computed proportion of the pre-tagged probable rDNA clusters exceeds a predetermined proportion.

10. The computer-implemented system as claimed in claim 9, wherein the plurality of modules stored in the memory includes an identification module further configured to:

compare the distance between the query vector and the cluster centroid of each of the plurality of reference clusters with the threshold distance; and
    select a reference cluster as a target cluster, when the distance between the query vector and the cluster centroid is greater than the threshold distance.

11. The system as claimed in claim 10, wherein the identification module is further configured to:
    identify a target cluster, from among the one or more target clusters, pre-tagged as a probable rDNA cluster; and
    compute a proportion of the one or more target clusters pre-tagged as the probable rDNA clusters to determine the proportion of the probable rDNA clusters.

12. The system as claimed in claim 10, wherein the plurality of modules stored in the memory include a cluster creation module configured to classify a plurality of reference sequences into the plurality of reference clusters, based on similarity in at least one compositional characteristic of the plurality of reference sequences.

13. The computer-implemented system as claimed in claim 9, wherein the plurality of modules stored in the memory includes an identification module further configured to:
    identify a reference cluster at a minimum distance from the query vector, based on computed distances, the one or more reference clusters comprising the identified reference cluster;
    determine a sequence count of the identified reference cluster; and
    compare the sequence count with the threshold sequence count;
    select the identified reference cluster as a target cluster, when the sequence count is greater than or equal to the threshold sequence count;
    iteratively identify one or more next closest reference clusters, based on the computed distances, wherein the one or more reference clusters comprise the identified reference cluster and the one or more next closest reference clusters, and wherein the one or more next closest reference clusters are identified till a cumulative sequence count of the one or more reference clusters is greater than or equal to the threshold sequence count; and
    select the one or more reference clusters as the target clusters, when the cumulative sequence count is greater than or equal to the threshold sequence count.

14. A non-transitory computer readable medium having computer executable instructions which when executed, implement a method for pre-tagging a subset of reference clusters from amongst a plurality of reference clusters as probable rDNA clusters and using information obtained from pre-tagging for identification of ribosomal deoxyribonucleic acid (rDNA) sequences from a sample containing a plurality of unknown DNA sequences, the method comprising:
    performing a rDNA analysis to pre-tag said plurality of reference clusters from amongst the plurality of reference clusters as said probable rDNA clusters, wherein the rDNA analysis comprises:
        obtaining a plurality of reference rDNA sequences from the reference database;
        generating a plurality of rDNA vectors corresponding to a plurality of reference rDNA sequences;
        computing a frequency of hits of each of said plurality of reference clusters corresponding to said plurality of reference rDNA sequences, wherein the frequency of hits is computed based on at least one of a threshold distance and a threshold sequence count;

comparing for each of the plurality of reference clusters, the computed frequency of hits with a predetermined frequency;
pre-tagging said subset of reference clusters from said plurality of reference clusters as the probable rDNA cluster, when the computed frequency of hits exceeds the predetermined frequency;
identifying a plurality of ribosomal deoxyribonucleic acid (rDNA) sequences from a sample containing a plurality of unknown DNA sequences based on the information obtained from pre-tagging, wherein the identifying includes:
creating a plurality of query sequences corresponding to said plurality of unknown DNA sequences by sequencing genetic material obtained from the sample;
computing a distance between a query vector corresponding to beach query sequence and a cluster centroid of each of a plurality of reference clusters, wherein each of the plurality of reference clusters includes said plurality of reference sequences, and wherein said plurality of reference sequences with similar composition are classified into at least one reference cluster;
selecting one or more target clusters corresponding to the query sequence from the plurality of reference clusters, wherein the one or more target clusters are selected based on
a comparison of the distance of each of the plurality of reference clusters with the threshold distance; and
a comparison of a cumulative sequence count of the plurality of reference clusters with the threshold sequence count;
computing the proportion of pre-tagged probable rDNA clusters within the one or more target clusters; and
identifying the query sequence as a rDNA sequence, when the computed proportion of the pre-tagged probable rDNA clusters exceeds a predetermined proportion.

15. The non-transitory computer readable medium as claimed in claim 14 further comprising classifying a plurality of reference sequences, into the plurality of reference clusters, based on similarity in at least one compositional characteristic of the plurality of reference sequences.

16. The non-transitory computer readable medium as claimed in claim 14, for identifying the one or more probable rDNA clusters further comprises instructions for:
generating a plurality of rDNA vectors corresponding to a plurality of reference rDNA sequences;
computing a frequency of hits of each of the plurality of reference clusters with respect to the plurality of the reference rDNA sequences, wherein the frequency of hits is computed based on the threshold distance and the threshold sequence count;
comparing, for each of the plurality of reference clusters, the frequency of hits with a predetermined frequency; and
pre-tagging a reference cluster from the plurality of reference clusters as a probable rDNA cluster, when the frequency of hits is in excess to the predetermined frequency.

17. The non-transitory computer readable medium as claimed in claim 14, further comprising instructions for computing proportion of pre-tagged probable rDNA clusters, wherein the computing comprises:
identifying number of target clusters, pre-tagged as probable rDNA clusters; and
comparing the number of the one or more identified target clusters pre-tagged as the probable rDNA clusters with the number of target clusters.

* * * * *